United States Patent [19]

Feld

[11] Patent Number: 4,764,638

[45] Date of Patent: Aug. 16, 1988

[54] METHOD FOR THE PREPARATION OF 2,6-NAPHTHALENE DICARBOXYLIC ACID

[75] Inventor: Marcel Feld, Cologne, Fed. Rep. of Germany

[73] Assignee: Dynamit Nobel AG, Cologne, Fed. Rep. of Germany

[21] Appl. No.: 896,116

[22] Filed: Aug. 12, 1986

[30] Foreign Application Priority Data

Aug. 16, 1985 [DE] Fed. Rep. of Germany ....... 3529381
Dec. 12, 1985 [DE] Fed. Rep. of Germany ....... 3543879

[51] Int. Cl.$^4$ .......................................... C07C 51/255
[52] U.S. Cl. ................................... 562/416; 562/413; 562/421
[58] Field of Search ...................... 562/416, 421, 413

[56] References Cited

U.S. PATENT DOCUMENTS 3,856,855 12/1974 Yamashita et al. ................. 562/416
4,665,215 5/1987 Davenport ...................... 562/421 X

FOREIGN PATENT DOCUMENTS 0170483 2/1986 European Pat. Off. ............ 562/421

Primary Examiner—Michael L. Shippen
Attorney, Agent, or Firm—Felfe & Lynch

[57] ABSTRACT

Disclosed is a method for the preparation of 2,6-naphthalene dicarboxylic acid from 2-acyl-6-alkyl naphthalene, especially 2-acetyl-6-methylnaphthalene, by oxidation in two steps with oxygen or air. The catalyst in the first oxidation is based on manganese. The catalyst in the second oxidation is based on cobalt with bromine added. The addition of 6-alkyl-2-naphthoic acid to the reaction in the second oxidation, in portions or in a continuous manner, results in very good yields having high purities.

22 Claims, No Drawings

METHOD FOR THE PREPARATION OF 2,6-NAPHTHALENE DICARBOXYLIC ACID

BACKGROUND OF THE INVENTION

The present invention relates to a method for the preparation of 2,6-naphthalene dicarboxylic acid, setting out from a 2-acyl-6-alkyl naphthalene, preferably 2-acetyl-6-methylnaphthalene, by a two-step oxidation with oxygen.

According to the invention, a 2-acyl-6-alkyl naphthalene is first oxidized with oxygen or an oxygen-containing gas, preferably air, in a first oxidation under the catalytic action of a manganese compound in an aliphatic carboxylic acid, preferably acetic acid, as solvent, or in a solvent containing an aliphatic carboxylic acid, and the oxidation product thus formed is oxidized with oxygen or a gas containing oxygen, preferably air, in a second oxidation, this time in the presence of a cobalt compound and a bromine compound as catalyst, in an aliphatic carboxylic acid as solvent, or in a solvent mixture containing an aliphatic carboxylic acid, preferably acetic acid, to form 2,6-naphthalene dicarboxylic acid.

The subject matter of the invention is a method for the preparation of 2,6-naphthalene dicarboxylic acid by oxidation in liquid phase with oxygen or an oxygen-containing gas, wherein the 2-acyl-6-alkyl naphthalene is oxidized in a first oxidation in the presence of a manganese compound which is soluble in the reaction mixture as catalyst, in an aliphatic carboxylic acid as solvent, or in a solvent mixture containing an aliphatic carboxylic acid, at temperatures of 80 to 180° C., and the 6-alkyl-2-naphthoic acid that forms is oxidized to the product in a second oxidation in the presence of a cobalt compound soluble in the reaction mixture and a component supplying bromine ions, as catalyst, in an aliphatic carboxylic acid as solvent, or in a solvent mixture containing an aliphatic carboxylic acid, at a reaction temperature of 150° to 250° C.

An important difference between the first and second oxidations of the method according to the invention thus has to do with the catalysts used. In the first oxidation a manganese catalyst is necessary. In the second oxidation, however a cobalt component and a bromine component are necessary as the catalyst. Optimally, a manganese compound can be used in the second oxidation in addition to the cobalt and bromine compound, but this is not necessary.

A number of methods are already known for the preparation of 2,6-naphthalene dicarboxylic acid suitable for the production of special polymers. Most of the methods set out from 2,6-dialkyl naphthalenes, especially 2,6-dimethylnaphthalene. The preparation of the starting products in the necessary isomeric purity, however, presents considerable difficulty. Also, the results of oxidations with atmospheric oxygen are unsatisfactory with regard to the yield and purity of the target products in the majority of the methods described in DE OS No. 21 07 357, Japan Kokai No. 76 06.953, Japan Kokai No. 77 17,453, or Belgian Patent No. 660,333.

In the method according to the invention, it is not dialkyl naphthalene that is used as the starting product, but a 2-acyl-6-alkyl naphthalene, especially 2-acetyl-6-methylnaphthalene, obtainable by the acylation of an alkyl naphthalene.

As will be shown by prior-art examples A and B, the conditions commonly used for the oxidation of alkyl aromatic compounds, including dialkyl naphthalenes, for example, and characterized by a combination of a cobalt and bromine compound as catalyst, are not well suited for the oxidation of such compounds with atmospheric oxygen in acetic acid solution. Instead, the oxidation conditions according to the invention are necessary in order to prepare 2,6-naphthalene dicarboxylic acid from a 2-acyl-6-alkyl naphthalene with superior results.

Suitable starting substances for the preparation of 2,6-naphthalene dicarboxylic acid by the method according to the invention are 2-acyl-6-alkyl naphthalenes of general Formula I:

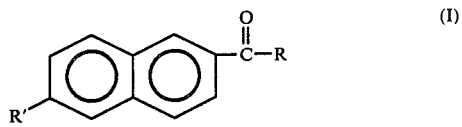

wherein R and R' represent identical or different, straight-chain or branched alkyl groups of 1 to 6 carbon atoms, in which the aromatic moiety in R' or the carbon atom nearest the carbonyl group in R must carry at least 1 hydrogen atom. The preferred starting product is 2-acetyl-6-methylnaphthalene ($R=R'=CH_3$). The starting substances are accessible through Friedel-Crafts acylation from alkyl naphthalene, especially 2-methylnaphthalene.

It is characteristic of the method of the invention that it involves two oxidations which are very different as regards their conditions. The first oxidation is catalyzed by a manganese compound in the absence of any cobalt compound and/or bromine compound. The preferred concentration of the manganese catalyst amounts to 0.001 to 0.1, preferably 0.01 to 0.05 parts by weight, per weight-part of the acyl alkyl naphthalene, in the form of a manganese compound that is soluble in the reaction mixture, examples being manganese (II) acetate or manganese(II) acetylacetonate. In the first oxidation, the cobalt component or the bromine component can be present, if desired, in the concentration suitable for the second oxidation, but not the two components simultaneously. But a manganese catalyst in the absence of bromine component is preferred.

Suitable solvents for the oxidation of acylated alkyl naphthalene according to the invention are aliphatic carboxylic acids having preferably 2 to 4 carbon atoms, especially acetic acid and/or the anhydrides of the aliphatic carboxylic acids, especially acetic anhydride. The aliphatic carboxylic acids or the corresponding anhydrides can be used alone, in combination with one another, or also in combination with an additional solvent which is stable against oxygen under the reaction conditions. A very suitable solvent is, in addition to pure acetic acid, a water-diluted acetic acid containing, for example, 1 to 20% water by weight.

The acylated alkyl naphthalene and the solvent or solvent mixture are used in the method according to the invention preferably in weight ratios of approximately 1:2 to 1:20 especially 1:3 to 1:10.

After separating from the reaction mixture such low-boiling components as water and/or formic acid, or after the addition of more solvent, if desired, but without isolating the reaction product formed from the acylated alkyl naphthalene, the reaction mixture obtained in the first oxidation can be further oxidized in the second oxidation after adding a suitable cobalt compound and a bromine compound. Preferably, the reaction product formed in the first oxidation from the acylated alkyl naphthalene can be isolated by a conventional solid-liquid separation, preceded in some cases by concentration or in others by dilution of the reaction mixture, by adding water for example, before it enters the second oxidation. Then the mother liquor obtained in the product isolation can be reused as a reaction medium for the oxidation of the acylated alkyl naphthalene. In this manner the yield is considerably increased, especially when the mother liquor is repeatedly reused. It is desirable first to remove water and other low-boiling components and, if necessary, to replace any losses of acetic acid and catalyst.

The first oxidation of the process is performed at a temperature of 80° to 180° C., preferably 100° to 160° C. The pressure amounts to 0 to 60 bar, preferably 5 to 40 bar.

The use of the manganese catalyst is essential to the first oxidation of the method according to the invention.

The second oxidation, however, is characterized by the use of a catalyst combination of a cobalt compound and a bromine compound. Suitable cobalt compounds are especially cobalt bromide, cobalt acetate, or a compound supplying cobalt acetate in an acetic acid solution. In addition to cobalt bromide, suitable bromine components are also elemental bromine, hydrogen bromide, acetyl bromide, and especially alkali bromides or ammonium bromide. It is essential that the bromine component be capable of forming bromine atoms or bromine ions under the conditions of the reaction.

The suitable catalyst concentration per weight-part of the acylated alkyl naphthalene put into the first oxidation, and of the oxidation product formed and, in some cases, isolated, and used in the second oxidation, amounts to 0.0005 to 0.05, preferably 0.002 to 0.02 weight-parts of cobalt in the form of a cobalt compound that is soluble in the reaction mixture, and 0.001 to 0.1, preferably 0.002 to 0.04 weight-parts of bromine in the form of a suitable bromine compound. Manganese does not interfere with the reaction performed in the second oxidation.

The preferred solvent for the second oxidation is also acetic acid or a water-diluted acetic acid. Suitable concentration ratios are approximately 2 to 50, preferably 4 to 20, parts of acetic acid by weight for each part by weight of the product to be oxidized.

The reaction temperature of the second oxidation is 150° to 250° C., preferably at 160° to 220° C. The temperature is preferably 20° to 80° C., especially 30° to 50° C., higher than in the first step. The pressure is 5 to 80 bar, preferably 10 to 60 bar.

The 2,6-naphthalene dicarboxylic acid resulting after the second oxidation can be isolated from the reaction mixture by a conventional solid-liquid separation.

Mother liquors of the second oxidation can be reused in the same manner for another oxidation of the second type, thereby increasing the yields, reducing the catalyst requirement, and greatly diminishing the cost of working up the mother liquor.

This two-step process brings about a considerable improvement over the one-step processes in comparison with one-step processes. For high purities of over 97%, large amounts of solvent are necessary in the second oxidation, such as 13 to 50 weight-parts per weight-part of alkylnaphthoic acid. Such high degrees of dilution in a technical process, however, are difficult when large amounts of filtrate have to be purified by distillation for reuse as a reaction medium or for the recovery of the acetic acid.

If the amount of solvent is great, the reactor has to be large, or smaller amounts will be produced in the same amount of time.

It has furthermore been found that the purity of 2,6-naphthalene dicarboxylic acid obtained under otherwise equal conditions diminishes greatly if the amount of the solvent is reduced. For example, in the case of a weight-ratio of the acetic acid solvent to the methylnaphthoic acid of 12:1 in the starting mixture, the target product was obtained in a purity of only 90.3%. The main impurity in the oxidation product was 6-formyl-2-naphthoic acid, plus the 6-methyl-2-naphthoic acid starting substance. If the input amount of 6-methyl-2-naphthoic acid was further increased, the 2,6-naphthalene dicarboxylic acid was obtained with a purity of only 87%.

2,6-naphthalene dicarboxylic acid should be prepared in the highest possible purity by oxidation of 6-alkyl-2-naphthoic acid at the highest possible ratio of 6-alkyl-2-naphthoic acid to the aliphatic carboxylic acid used as solvent.

In a further embodiment of the invention, therefore, 2,6-naphthalene dicarboxylic acid is prepared by adding the alkylnaphthoic acid to the reaction mixture entirely or largely in the course of the reaction. Therefore, to achieve a target product of comparable or better purity in the same amount of the solvent, a considerably greater amount, even several times the amount, of a 6-alkyl-2-naphthoic acid is oxidized, if not all of it is in the starting mixture, but is added for the most part while the reaction is in progress. This addition can be performed in portions or, advantageously, in a continuous manner, and can be adapted approximately to the rate of the reaction.

The first oxidation can also be performed in this manner.

The alkyl naphthoic acid can be added in solid form, or else can be suspended or dissolved in a suitable, oxidation-resistant solvent, preferably in the aliphatic carboxylic acid of 2 to 4 carbon atoms used as the reaction medium.

In the case of the proportioning of a solution of the alkylnaphthoic acid, e.g., in acetic acid and/or acetic anhydride, the solution can be prepared and added at elevated temperature—at the reaction temperature for example. Preferred, however, are suspensions of the starting substance in the solvent, up to the fluidity limit.

The effect on purity that is produced by the addition of the largest possible quantities of the starting substance per quantity of solvent, continuously or in frequent small portions, is surprisingly high, and can be demonstrated by dividing the oxidation arbitrarily into individual sections, with portions of the given amount of alkylnaphthoic acid to be oxidized in each case.

In technical production, the starting substance is added continuously or approximately continuously in the form of a highly concentrated suspension, even in solid form in some cases, as the reaction proceeds.

At the start of the reaction, a proportion in the mixture of 5 to 10% of the total amount of alkylnaphthoic acid to be oxidized is sufficient, although even greater amounts—25% for example—are possible. Single portions added should not be greater than 25%. Under these conditions, the total amount can advantageously amount to 0.1 to 0.6 weight-parts per weight-part of solvent.

EXAMPLES

Example 1

First Oxidation

A Hastelloy C autoclave equipped with heater, stirrer, gas introduction tube, temperature sensor, pressure gauge and pressurized reflux condenser was charged with 100 g of 2-acetyl-6-methylnaphthalene, 380 g of acetic acid, 20 g of water and 15 g of manganese(II) acetate. Compressed air was passed, with stirring, through the solution at 140° C. and a pressure of 25 bar, with a gas escape rate of 3 liters per minute. The reaction was observed by continuously measuring the oxygen content in the exhaust gas. When this oxygen content returned to the initial level of 21% after a reaction time of 105 minutes, the air feed was shut off, the reaction mixture was cooled, with stirring, to room temperature, filtered, and the filter cake washed with 300 g of a 95 wt.-% solution of acetic acid. 70.3 g of 6-methyl-2-naphthoic acid (69.3% of the theory) was obtained, in a purity of 99.5%.

The mother liquor combined with the wash filtrates was concentrated to 380 g by distilling out water, formic acid and acetic acid. After the addition of 20 g of water, 67.5 g of 2-acetyl-6-methylnaphthalene and 3.5 g of manganese(II) acetate was again oxidized under the conditions described above. This time 67.3 g of 6-methyl-2-naphthoic acid (98.2% with respect to freshly input 2-acetyl-6-methylnaphthalene) was obtained.

Second Oxidation

By a procedure similar to that described above for the first oxidation, 36.5 g of the product isolated in that oxidation was oxidized in a solution of 2 g of cobalt acetate and 0.5 g of sodium bromide in 500 g of acetic acid at a temperature of 190° C., a pressure of 25 bar, and a gas escape rate of 4 liters per minute. After 140 minutes of reaction, the reaction mixture, cooled to room temperature, was filtered, the filter cake was washed with 250 g of acetic acid, and dried. 35.4 g of 2,6-naphthalene dicarboxylic acid (81.9%) was obtained with a purity of 97.9% as determined by gas chromatography.

The mother liquor combined with the wash filtrate was concentrated to a weight of 500 g by distilling out water and acetic acid, 0.2 g of sodium bromide and 35 g of the product isolated from the first oxidation were added, and then oxidized again under the conditions described above, and worked up. 36.2 g (86.9% of the theory) of 2,6-naphthalene dicarboxylic acid was obtained with a purity of 97.4%.

Example 2

A mixture of 50 g of 2-acetyl-6-methylnaphthalene, 380 g of acetic acid, 20 g of water and 7.5 g of manganese(II) acetate was oxidized at 140° C., 25 bar, and a air escape rate of 1.5 liters per minute. After oxygen absorption had ended, 5 g of cobalt acetate and 0.5 g of sodium bromide were added and air was bubbled through in the same manner at 190° C. After this second oxidation, 50.8 g of product with a content of 93% of 2,6-naphthalenedicarboxylic acid (80.8% of the theory) was isolated by working up the product as in Example 1.

Prior-Art Example A

With the experimental arrangement described in Example 1, 50 g of 2-acetyl-6-methylnaphthalene, 400 g of acetic acid, 5 g of cobalt acetate and 0.5 g of sodium bromide were used for the oxidation at 140° C., a pressure of 25 bar, and a gas escape rate of 2 liters per minute. 15.2 g of a product mixture containing only 30.9% of 2,6-naphthalenedicarboxylic acid was isolated by filtration from the reaction mixture cooled to room temperature after the absorption of oxygen had ended.

Prior-Art Example B

Prior-Art Example A was repeated at a reaction temperature of 190° C. This time only 14.7 g of solid containing 40% of 2,6-naphthalene dicarboxylic acid was isolated from the reaction mixture.

Prior-Art Example C

Prior-Art Example A was repeated with an additional 5 grams of manganese(II) acetate as catalyst component. 50.0 g of a product mixture containing 79.1% of 2,6-naphthalenedicarboxylic acid was isolated from the reaction mixture.

Example 3

The first oxidation described in Example 1 was repeated using a starting mixture of 50 g of 2-acetyl-6-methylnaphthalene, 300 g of acetic acid, 100 g of water and 7.5 g of manganese(II) acetate. 39.2 g of oxidation product was isolated from the reaction mixture by filtration. 20 g of this product was then oxidized in the second oxidation step described in Example 1, in a solution of 2 g of cobalt(II) acetate and 0.5 g of sodium bromide in 500 g of acetic acid, at 180° C. and a gas escape rate of 2 liters per minute. 18.7 g of 2,6-naphthalene dicarboxylic acid was then obtained from the reaction mixture, in a purity of 97.7%.

Example 4

As in Example 3, first a mixture of 50 g of 2-acetyl-6-methylnaphthalene, 400 g of acetic acid and 10 g of manganese(II) acetate is oxidized at 140° C. Of the 31.7 g of oxidation product then isolated, 10 g in a solution of 2 g of cobalt(II) acetate and 0.5 g of sodium bromide in 500 g of acetic acid was subjected to a second oxidation at 190° C. 9.6 g of 2,6-naphthalenedicarboxylic acid was then obtained in a purity of 97.7%.

Example 5

A Hastelloy C autoclave equipped with heater, stirrer, gas introduction tube, temperature sensor, pressure gauge and pressurized reflux condenser was charged with 25 g of 6-methyl-2-naphthoic acid (purity 96.8%), 1200 g of 95 wt.-% acetic acid, 8 g of cobalt(II) acetate tetrahydrate and 8 g of sodium bromide, heated under nitrogen at 185° C., and then air at a pressure of 25 bar is passed through the solution at a gas escape rate of 2 liters per minute, measured after expansion. The reaction was observed by continuously measuring the oxygen content in the exhaust gas; after the oxygen content thus measured had increased to 7%, the reaction was interrupted, another 25 g of 6-methyl-2-naphthoic acid of equal quality was added to the reaction mixture relieved of pressure at 100° C., and oxidation was again performed in the manner described above. The process was then repeated two more times, but after the last addition of methylnaphthoic acid the air feed was continued at 185° C. until the oxygen content in the exhaust gas had reached a level of 20%. The reaction mixture, cooled and relieved of pressure, was filtered, the filter cake washed with 400 g of acetic acid, and dried. The result was 105.3 g (91.5% of the theory) of 2,6-naphthalenedicarboxylic acid with a purity of 97.8%.

The mother liquor combined with the wash filtrate was concentrated by distillation to a weight of 1,230 g with a moisture content of 5% by weight, 25 g of 6-methyl-2-naphthoic acid of the quality described above and 2 g of sodium bromide were added and oxidized in the manner previously described, and then three more batches of 25 g of 6-methyl-2-naphthoic acid were oxidized. This time 108.7 g (94.5% of the theory) of 2,6-naphthalenedicarboxylic acid was obtained in a purity of 97.7%.

Example 6

In a manner similar to Example 5, first 25 g, and then a total of 188 g in eight equal portions, of 6-methyl-2-naphthoic acid (purity 97.6%) was oxidized in 1200 g of 97.5 wt.-% acetic acid under the reaction conditions and using the catalysts described in Example 1. The product was 230.8 g of a 97.9% 2,6-naphthalenedicarboxylic acid (93.6% of the theory).

Example 7

The experiment described in Example 5 was repeated with 120 g of 6-methyl-2-naphtoic acid in 12 portions of 10 g each. 131.6 g of naphthalene dicarboxylic acid was obtained in a purity of 98.9% (yield 96.5% of the theory).

Example 8

Example 5 was repeated, but with only 800 g of 95 wt.-% acetic acid and 10 g of 6-methyl-2-naphthoic acid (purity 96.2%) at the beginning, and with the addition of 100 g of starting substance in 400 g of the acetic acid in 20 substantially equal portions during the reaction. 118.8 g of product was obtained. Purity 99.1%, yield 95.8% of the theory.

It will be understood that the specification and examples are illustrative but not limitative of the present invention and that other embodiments within the spirit and scope of the invention will suggest themselves to those skilled in the art.

I claim:

1. A method for the preparation of 2,6-naphthalenedicarboxylic acid comprising: oxidizing a 2-acyl-6-alkyl naphthalene in liquid phase with oxygen or a gas containing oxygen, in the presence of a soluble manganese compound as catalyst, in an aliphatic carboxylic acid as solvent, or in a solvent mixture containing an aliphatic carboxylic acid, at temperatures of 80° to 180° C., to form as oxidation product a 6-alkyl-2-naphthoic acid; and oxidizing the 6-alkyl-2-naphthoic acid in the presence of a soluble cobalt compound and a component supplying bromine ions as catalysts, in an aliphatic carboxylic acid as solvent, or in a solvent mixture containing an aliphatic carboxylic acid, at a reaction temperature of 150° to 250° C. with oxygen or a gas containing oxygen.

2. The method of claim 1, wherein acetic acid or a water-diluted acetic acid is used as solvent in both oxidations.

3. The method of claim 1, wherein the 2-acyl-6-alkyl naphthalene is 2-acetyl-6-methylnaphthalene.

4. The method of claim 1, wherein, in the first oxidation, 0.001 to 0.1 to weight-parts of manganese in the form of a compound soluble in the reaction mixture is used in the first oxidation stage for each weight-part of the 2-acyl-6-alkyl naphthalene.

5. The method of claim 1, wherein the 2-acyl-6-alkyl naphthalene and the solvent are used in the weight ratio of 1:2 to 1:20.

6. The method of claim 1, wherein the first oxidation is performed at a temperature of 100° to 160° C. and a pressure of 5 to 60 bar.

7. The method of claim 1, wherein the first oxidation is performed in the absence of a bromine catalyst.

8. The method of claim 1, wherein, after the first oxidation, the oxidation product is isolated by a solid-liquid separation and mother liquor, after separation of water, formic acid, and any solvent additionally entering with wash filtrates, is again used as a reaction medium for the oxidation of 2-acyl-6-alkyl naphthalene.

9. The method of claim 1, wherein, for each weight-part of the 2-acyl-6-alkyl naphthalene used in the first oxidation, or of the oxidation product formed therefrom and isolated and used in the second oxidation, 0.0005 to 0.05 weight-parts of cobalt are used in the form of a cobalt compound that is soluble in the reaction mixture, and 0.001 to 0.1 weight-parts of bromine in the form of a substance supplying bromide ions under the reaction conditions.

10. The method of claim 1, wherein the oxidation product isolated after the first ocidation, and the solvent, are used in the second oxidation in the weight ratio of 1:2 to 1:50.

11. The method of claim 1, wherein the second oxidation is performed at a temperature of 150° to 250° C. and at a pressure of 5 to 80 bar.

12. The method of claim 1, wherein mother liquor obtained after separation of the 2,6-naphthalene dicarboxylic acid by a solid-liquid separation of the reaction mixture after the second oxidation is reused, after distillative separation of reaction water and of any solvents that may have entered with wash filtrates, as a reaction medium for the second oxidation.

13. The method of claim 1, wherein the 6-alkyl-2-naphthoic acid is added continuously in or in portions during the reaction in the second oxidation.

14. The method of claim 13, wherein a total of 0.1 to 0.4 weight-parts of the 6-alkyl-2-naphthoic acid is used per weight-part of solvent.

15. The method of claim 4 wherein 0.01 to 0.05 weight-parts of the manganese compound is used.

16. The method of claim 9 wherein the manganese compound is manganese (II) acetate and/or manganese (II) acetylacetonate.

17. The method of claim 5 wherein the weight ratio is 1:3 to 1:10.

18. The method of claim 9 wherein 0.002 to 0.02 weight-parts of cobalt are used.

19. The method of claim 9 wherein 0.002 to 0.04 weight-parts of bromine are used.

20. The method of claim 10 wherein the ratio is 1:4 to 1:20.

21. The method of claim 11 wherein the temperature is 160° to 220°C.

22. The method of claim 11 wherein the pressure is 10 to 60 bar.

* * * * *